US009326779B2

(12) United States Patent
Dorawa et al.

(10) Patent No.: US 9,326,779 B2
(45) Date of Patent: May 3, 2016

(54) SOFT TISSUE PROTECTOR AND DRILL GUIDE FOR AN IMPLANTATION KIT

(71) Applicant: Stryker Trauma SA, Selzach (CH)

(72) Inventors: Klaus Dorawa, Schoenkirchen (DE); Stefano Brianza, Basel (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 212 days.

(21) Appl. No.: 13/734,344

(22) Filed: Jan. 4, 2013

(65) Prior Publication Data

US 2013/0178860 A1    Jul. 11, 2013

(30) Foreign Application Priority Data

Jan. 6, 2012 (EP) .................................. 12150401

(51) Int. Cl.
*A61B 17/17* (2006.01)
*A61B 17/16* (2006.01)
*A61B 17/34* (2006.01)

(52) U.S. Cl.
CPC ............. *A61B 17/17* (2013.01); *A61B 17/1633* (2013.01); *A61B 2017/3464* (2013.01)

(58) Field of Classification Search
CPC ............... A61B 17/17; A61B 17/1728; A61B 17/1732; A61B 17/1739–17/1767; A61B 17/0206; A61B 17/0293; A61B 2017/1775–2017/1782; A61B 2017/1789; A61B 2017/1792
USPC ............ 606/86 R, 96–98, 104; 279/114, 115, 279/116, 71, 72, 73; 403/239 R, 240
See application file for complete search history.

(56) References Cited

U.S. PATENT DOCUMENTS

| 1,442,107 | A | * | 1/1923 | Vernaz | 279/114 |
| 1,799,019 | A | * | 3/1931 | Mischler | 279/123 |
| 2,181,746 | A | * | 11/1939 | Siebrandt | 606/96 |
| 2,435,439 | A |   | 2/1948 | Goodwin |  |
| 2,437,652 | A | * | 3/1948 | Reddick | 219/138 |
| 2,472,453 | A |   | 6/1949 | Wolf |  |
| 2,523,374 | A | * | 9/1950 | Jensen | 279/123 |

(Continued)

FOREIGN PATENT DOCUMENTS

| DE | 38 00 482 A1 | 7/1989 |
| EP | 2228158 A2 | 9/2010 |
| GB | 2450529 A | 12/2008 |

OTHER PUBLICATIONS

European Search Report for EP 12150401.3 dated Jul. 11, 2012.

*Primary Examiner* — Matthew Lawson
*Assistant Examiner* — Amy Sipp
(74) *Attorney, Agent, or Firm* — Lerner, David, Littenberg, Krumholz & Mentlik, LLP

(57) ABSTRACT

A drill guide for guiding elements, especially drill bits and implants of an implantation kit during a surgical intervention, has a main body having a gripping portion. The drill guide has an upper and a lower central opening along its longitudinal axis with a through going cavity for receiving the element to be guided. A lower contact surface is positioned on an object, such as a bone, on or into which the element is to be guided. The diameter of the through going cavity can be varied by a.) radial positioning of three or four jaws inside the cavity through a groove-slide block system and/or b.) against the force of a spring at the lower free end of guiding extensions. The spring is provided on the back side of the extensions which bear against the inner wall of the drill guide sleeve.

12 Claims, 10 Drawing Sheets

(56) References Cited

U.S. PATENT DOCUMENTS

| | | | | |
|---|---|---|---|---|
| 2,690,915 A | * | 10/1954 | Pealer | 279/114 |
| 3,097,891 A | | 7/1963 | Brideau | |
| 3,108,500 A | | 10/1963 | Merriman | |
| 3,128,768 A | * | 4/1964 | Geistauts | 606/180 |
| 3,248,120 A | * | 4/1966 | Volpe | 279/71 |
| 3,248,121 A | * | 4/1966 | Volpe | 279/71 |
| 3,516,680 A | * | 6/1970 | Andre | 279/4.12 |
| 3,891,171 A | * | 6/1975 | Samuelian et al. | 248/131 |
| 4,028,969 A | * | 6/1977 | Politte | 81/146 |
| 4,341,206 A | * | 7/1982 | Perrett et al. | 606/80 |
| 4,353,561 A | * | 10/1982 | Peterson | 279/123 |
| 4,431,202 A | * | 2/1984 | Swenson | 279/106 |
| 4,705,331 A | * | 11/1987 | Britton | 439/387 |
| 4,838,562 A | * | 6/1989 | Akashi | 279/106 |
| 5,054,733 A | * | 10/1991 | Shields | 248/313 |
| 5,154,380 A | * | 10/1992 | Risca | 248/154 |
| 5,186,515 A | * | 2/1993 | Goldberg et al. | 294/119.1 |
| 5,993,459 A | * | 11/1999 | Larsen et al. | 606/104 |
| 6,416,518 B1 | * | 7/2002 | DeMayo | 606/96 |
| 7,563,061 B2 | * | 7/2009 | Gibbons et al. | 408/240 |
| 8,292,305 B2 | * | 10/2012 | Chen | 279/114 |
| 2002/0087162 A1 | * | 7/2002 | McDowell et al. | 606/80 |
| 2003/0158553 A1 | | 8/2003 | Michelson | |
| 2005/0033301 A1 | * | 2/2005 | Lombardo et al. | 606/72 |
| 2005/0137606 A1 | * | 6/2005 | Binder et al. | 606/96 |
| 2010/0232897 A1 | | 9/2010 | Torrents I Comas | |
| 2011/0245833 A1 | | 10/2011 | Anderson | |

* cited by examiner

SOFT TISSUE PROTECTOR AND DRILL GUIDE FOR AN IMPLANTATION KIT

CROSS-REFERENCE TO RELATED APPLICATION

The present application claims priority from European Patent Application No. 12150401.3 filed Jan. 6, 2012, the disclosure of which is hereby incorporated herein by reference.

BACKGROUND OF THE INVENTION

The present invention relates to soft tissue protector and drill guide for guiding elements, especially drill bits and implants of an implantation kit during a surgical intervention, comprising a soft tissue protector main body having a gripping portion, wherein the drill guide has an upper and a lower opening along its longitudinal axis with a through going cavity for receiving the element to be guided, and a lower object contact surface to be positioned on an object on or into which said element is to be guided, wherein the diameter of the through going cavity can be varied.

Drilling and positioning implants in bones require protection of the surrounding soft tissues. In the prior art this is achieved through hollow cylindrical metallic parts that prevent contact between the instrument or implant and the surrounding soft tissues. These same tools are produced in different diameters in order to accommodate for different drill bits and implants diameters.

The soft tissue protector can be also used to roughly guide the surgeon in achieving determined alignments between implants. Several of these soft tissue protectors can be joined through a metallic connector and help the surgeon drilling concentric holes and maximizing the implant grip in the bone.

The use of implants having many different diameters requires the surgical sets to be equipped with a considerable number of parts. These are the drills necessary to perform adequate holes and the chucks necessary to join the drill bits to the drill, different trocars and sleeves. For using 3, 4, 5 and 6 millimeter pins, e.g. twelve different parts can be necessary. A large number of parts require the surgeon and the assistants to pay additional attention in selecting the proper equipment. Furthermore, so many parts result in a heavier and larger instruments tray.

A drill guide and soft tissue protector is known from U.S. Patent Application Publication No. 2010/0232897. This drill guide has a main body with a flat base and an aperture for assisting the movement of the drill bit. Interchangeable drilling heads adapted to guide drill bits of different diameters are provided and can be positioned inside the housing of the main body wherein the drilling heads are maintained in the housing by a retention plate. The device can be held by the user at the handle.

BRIEF SUMMARY OF THE INVENTION

Based on this prior art, it is one aspect of the present invention to provide a soft tissue protector guide being adapted for aiming different diameter drill bits and implants; saving surgical time during implant insertion; decreasing soft tissue injury during surgery and decreasing the number of parts a surgeon needs to manipulate for standard surgical procedures.

It is a further aspect of the invention to improve positioning of implants of different sizes using a single tool as tissue protector.

The above mentioned goals are achieved through a soft tissue protector and drill guide for guiding elements of an implantation kit during a surgical intervention. The drill guide includes a soft tissue protector main body, a gripping portion attached at the soft tissue protector main body, a rotatable adjustment cap mounted on the main body and a plurality of jaws defining a through going cavity along the longitudinal axis of the soft tissue protector main body. The jaws have inner jaw surfaces, wherein the through going cavity has an upper and a lower opening for receiving the element to be guided, wherein the jaws engage the adjustment cap as well as the soft tissue protector main body. The soft tissue protector main body has a lower contact surface to be positioned on a bone on or into which a bone screw is to be guided. The diameter of the through going cavity can be varied. The adjustment cap can be rotated against the soft tissue protector main body forcing the jaws radially apart providing the variable diameter of the through going cavity with their inner jaw surfaces. The elements of an implantation kit are drill bits and implants. Each jaw comprises a flexible guiding extension ending near the lower opening of the drill guide. The flexible guiding extension comprises, at the free end of the guiding extension, a guide spring oriented away from the longitudinal axis of the guiding extension, contacting the inner wall of the drill guide sleeve and pushing the inner jaw surfaces of the flexible guiding extension one against the other. This allows passage of the elements against the action of the spring. Each jaw comprises a stiff upper jaw body being radially guided in the drill guide body and connected to the flexible extension. Each upper jaw body comprises a first guide, wherein the tissue protector main body comprises a complementary second guide for each first guide of the upper jaw body, allowing for a radial movement of the upper jaw body upon rotation of the main body against the jaws. The first guide may be slide blocks and the complementary second guide are spiral grooves extending from an inner position end to an outer position of each groove end each groove adapted to receive a slide block of one jaw body. Each upper jaw body comprises a rotating element, wherein the adjustment cap provides the upper opening and comprises complementary rotation element for each rotating element of the jaws engaging them for providing a rotation of the jaw bodies against the tissue protector main body when the cap is rotated. The rotating element is a pin and the complementary rotation element for each pin is a radially oriented slot engaging each pin for allowing the radial movement of the jaw during a rotation of the jaw bodies. The soft tissue protector and drill guide may comprise at least three jaws. In the innermost position the walls of adjacent jaw bodies contact each other, thus providing a completely surrounded inner through going cavity.

Thus the soft tissue protector and drill guide for guiding elements, especially drill bits and implants such as bone screws of the implantation kit during an surgical intervention, includes a soft tissue protector main body having a gripping portion. The drill guide has an upper and a lower opening along its longitudinal axis with a through going cavity for receiving the element to be guided, and a lower object contact surface to be positioned on an object on or into which said element is to be guided. The diameter of the through going cavity can be varied. The soft tissue protector and drill guide comprises a number of jaws engaging an adjustment cap as well as engaging the main body, wherein the adjustment cap can be rotated against the main body forcing the jaws radially apart providing the variable diameter of the through going cavity with their inner jaw surface.

It is an advantage for a centered guiding of elements like drills into a guide, where each jaw comprises such a flexible guiding extension ending near the lower opening of the drill guide. Each flexible guiding extension comprises, at the free end of the guiding extension, a guide spring oriented away from the longitudinal axis of the guiding extension. The spring contacts the inner wall of the drill guide sleeve and pushes the inner jaw surfaces of the flexible guiding extension one against the other, allowing passage of drill or implant elements against the action of the spring, which elements are readily centered from the beginning of the introduction.

The mechanism according to the invention allows concentric translation of different planes aimed to orient drill bits of different diameters along the same axis and driving the drills and implants during insertion and protecting the soft tissues. The concentric translation of the planes is driven by the mechanism of the present invention to determined positions. The features of the mechanism allow for the planes stability in each position to drive a drill bit or to drive the insertion of a surgical implant. The mechanism is designed that it can be easily disassembled and cleaned.

A drill guide or other element lower contact surface is therefore positioned on an object, such as a bone, on or into which the element is to be guided, wherein the diameter of the through going cavity can be varied by a.) positioning of four jaws inside the cavity and/or b.) against the force of a spring at the lower free end of the guiding extension provided on the back side of the extension against the inner wall of the drill guide sleeve.

The user of the device applies a method for adapting the diameter of the drill guide to a specific drill he intends to use, comprising the method steps of:

providing a soft tissue protector and drill guide for guiding elements according to the invention, turning the adjustment cap mounted on the main body in a direction, engaging the jaws which turn and move radially apart providing the maximum adaptable diameter of the through going cavity with their inner jaw surface for the upper jaw bodies, introducing the element to be guided through the upper predefined opening of the adjustment cap through the through going cavity with the inner jaw surface, and rotating the adjustment cap in the opposite direction to close the jaws on the element to be guided.

It is especially advantageous that the step of introduction comprises an advancement of the element to be guided into the extension portions of the jaws which are closed to the minimum diameter at the lower free ends until they are pushed one away from the other by the introduction of the element to be guided against the force of spring elements on the backside of the flexible guiding extension, allowing the passage of said elements against the action of the spring being biased against the inner wall of the drill guide sleeve.

A further aim of the springs is to provide the moving flat surfaces support where they are thinner and then it is not intended that the distal portion of the lower surfaces exert an important force radial to the drill because this could make the drill extraction difficult.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

BRIEF DESCRIPTION

Figure 1:
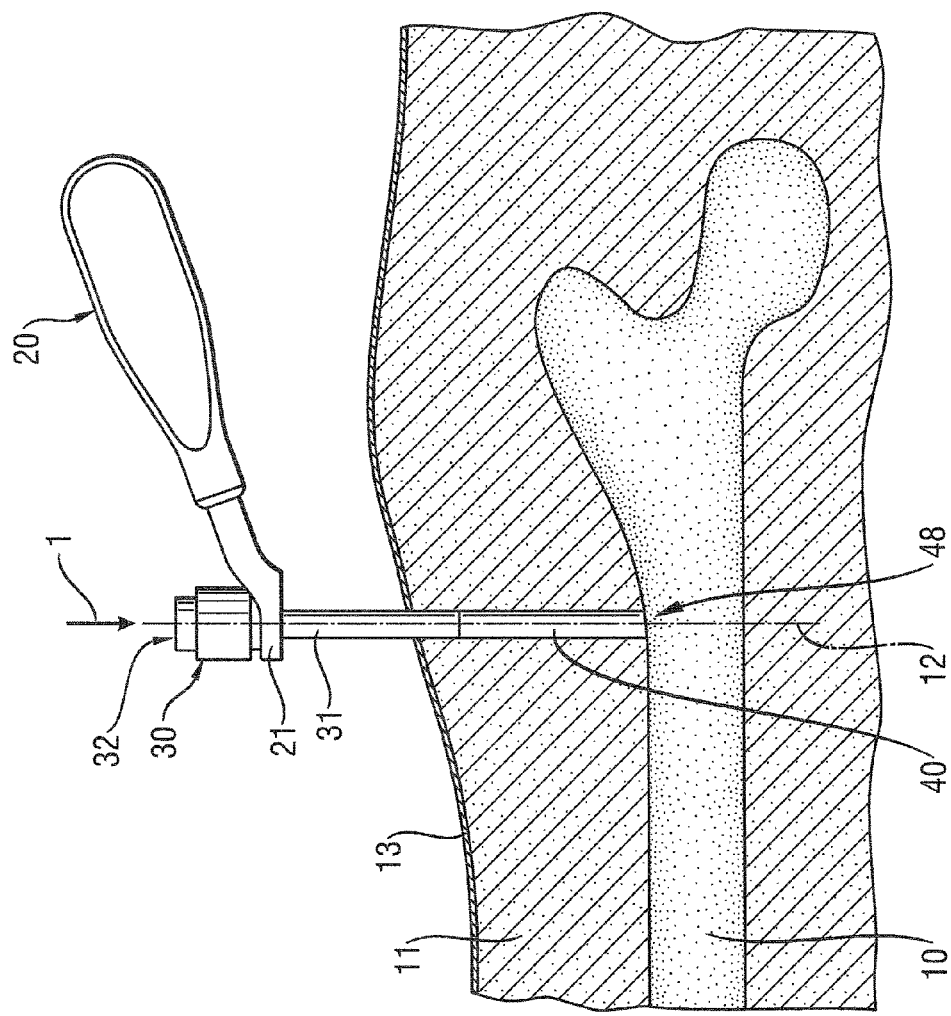
FIG. 1 shows a schematic side view of a bone within a limb and the application of a soft tissue protector and drill guide according to the invention.

FIG. 1 shows a schematic side view of a bone 10 within a limb (such as a leg) of a patient and the application of a drill guide according to an embodiment of the invention, having received the reference numerals 20, 30, 40 for different parts of the guide. A surgeon intents to drill a hole along the longitudinal axis 12 of the guide or to insert an implant into the bone 10 along axis 12. The bone 10 is covered by subcutaneous tissue 11 which is separated to the environment by the skin 13 of the patient. The schematic representation of FIG. 1 does not show how the area of the bone 10 is actually reached by the drill guide. The bone 10 is reached through standard surgical access, a skin stab incision and soft tissue dissection. The schematic representation shows a drill guide head 30 which is attached to a handle 20 wherein a drill guide sleeve 31 extends beyond the handle attachment flange 21 and is oriented along the longitudinal axis 12 into the subcutaneous tissue 11. It is possible that the drill guide sleeve 31 directly contacts the bone 10. In the representation of FIG. 1 an extension 40 is provided and connected with the drill guide sleeve 31.

Figure 2:
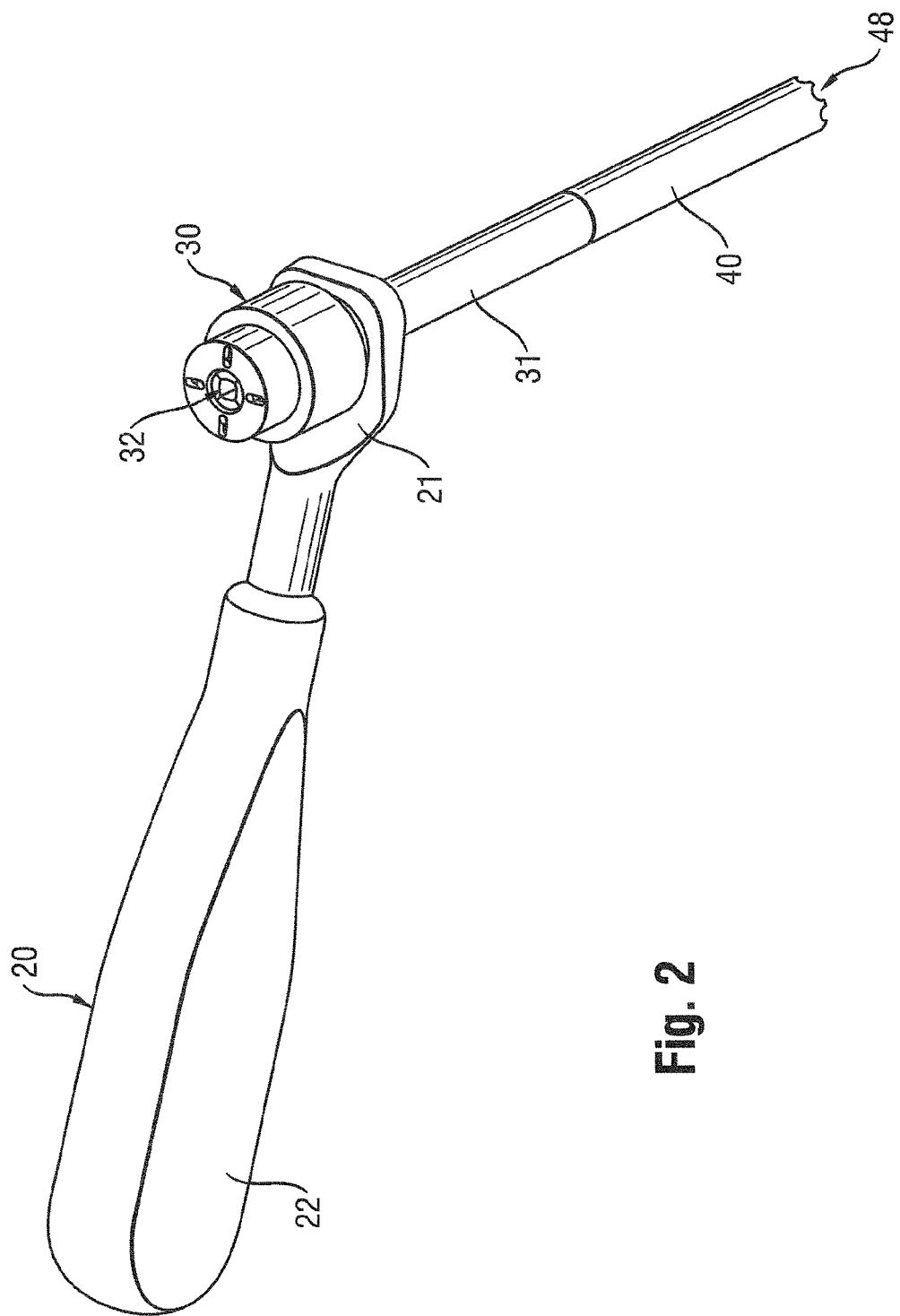
FIG. 2 shows a perspective view of the drill guide according to the embodiment shown in FIG. 1.

FIG. 2 shows a perspective view of the drill guide according to the embodiment shown in FIG. 1. Same reference numerals are used for identical or for similar features. The handle 20 comprises a grip 22 which is oriented at an obtuse angle in relation to the handle attachment flange 21. Thus the axis of handle 20 and axis 12 of drill guide sleeve 31 forms the obtuse angle. Handle attachment flange 21 is a flat and rounded element with an internal opening to receive the parts of the drill guide. This enables a simple cleaning of the different parts. In a top view shown in FIG. 3 the handle attachment flange 21 is almost square with rounded edges. The central opening is circular/square or polygonal.

The drill guide head 30 extends above the handle attachment flange 21 whereas the drill guide sleeve 31 is fitted into the handle attachment flange 21. As can be seen from FIG. 2 the drill guide head 30 has an upper opening 32 provided to allow reception of a drill bit or an implant along axis 12.

Figure 3:
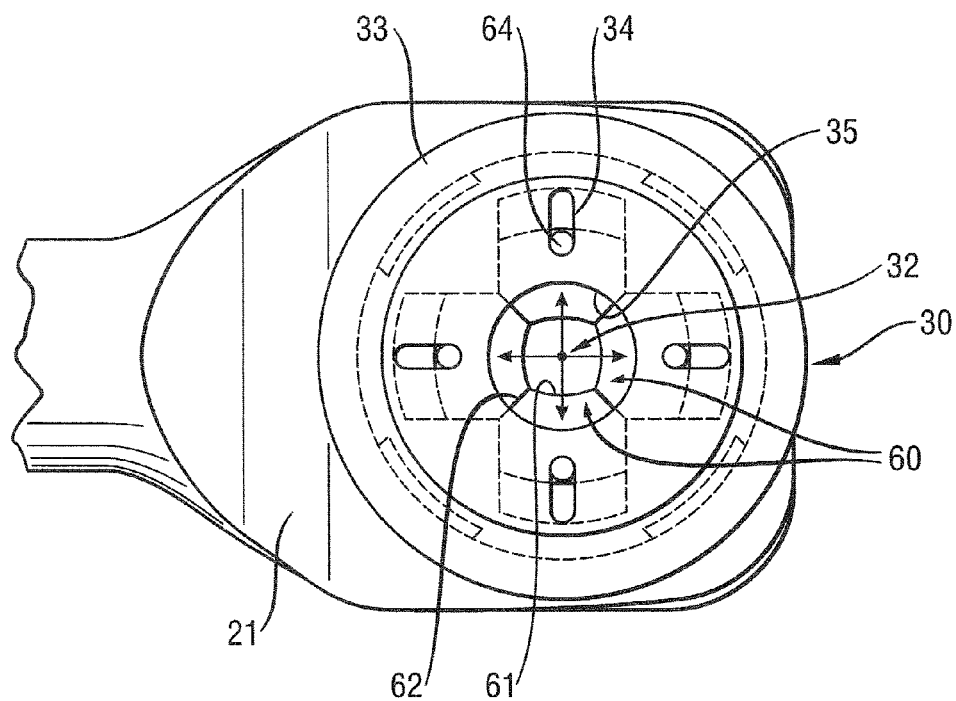
FIG. 3 shows a view from above on the drill guide head of the drill guide of FIG. 2.

FIG. 3 shows a drill guide head 30 and flange 21 of the drill guide of FIG. 2 viewed from above. The reference numeral indicates the inner edge of the bore or opening 32 and therefore defines the largest drill bit or implant which can be introduced into the opening 32. Several parts of the drill guide head 30 are shown being below an upper cover. The drill guide head 30 is fitted into the opening 32 and fitted together to rotate together with respect to sleeve 31 around axis 12. Drill guide sleeve 31 is fixed to attachment flange 21. The angular displacement of drill guide head 30 influences the opening 32 and determines the angular displacement of four jaw parts 60. When these jaws 60 rotate, each notch 66 displaces the corresponding part 60 to a different radial distance from axis 12. An adjustment sleeve or adjustment cap 33, which is rotatable against a drill guide plate 70 (shown in FIG. 5) is shown partly in a transparent view to explain the bearing of the four jaws 60.

The internal form of the guide cavity 49 (FIG. 6) and the related surfaces are generated by the internal surfaces 61 of four jaws 60, positioned around the central axis 12. It is also possible, according to other embodiments, that three or five jaws 60 are provided. As the view of above of FIG. 3 provides a kind of cross-section, it can be seen, that the curvature of the inner jaw surface 61 is less or equal to the curvature of the inner edge 35 of opening 32. In other words the virtual radius of the inner jaw surface 61 is larger than the radius of the circle provided by the inner edge 35. It is preferred that opening 35 and the maximum diameter allowed for a given application provided by the jaws 60 are equal.

The four jaws 60 each covering 90 degree of the walls of the internal cavity 49 are shown in FIG. 3 in there innermost position, in which the contacting jaw surfaces 62 on each side of the jaws 60 touch each other and therefore define the smallest possible guide surface. This can also be seen from the jaw actuating pins 64 which are provided on the outer side of the jaws 60 at their upper surface which are located at the inner end of the oblong guide slots 34.

Figure 4:
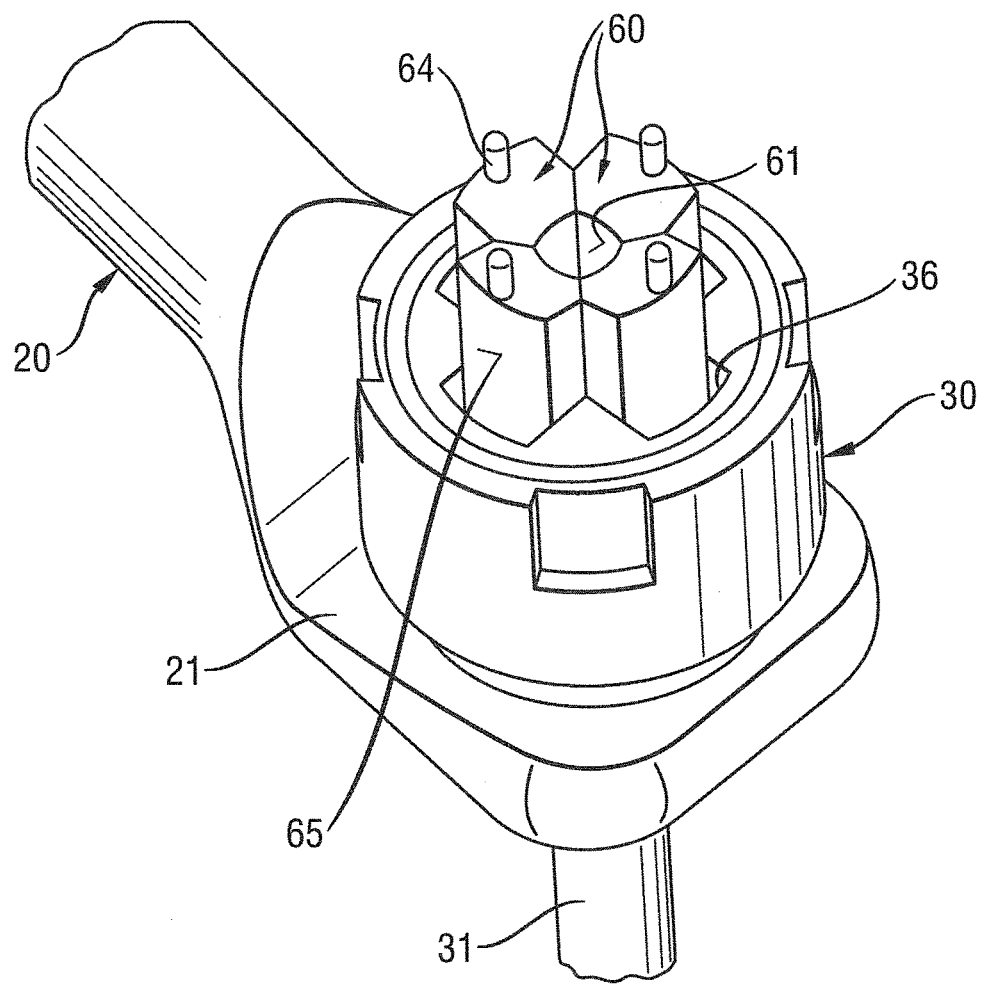
FIG. 4 shows a perspective view of a partly opened drill guide of FIG. 2.
Figure 5:
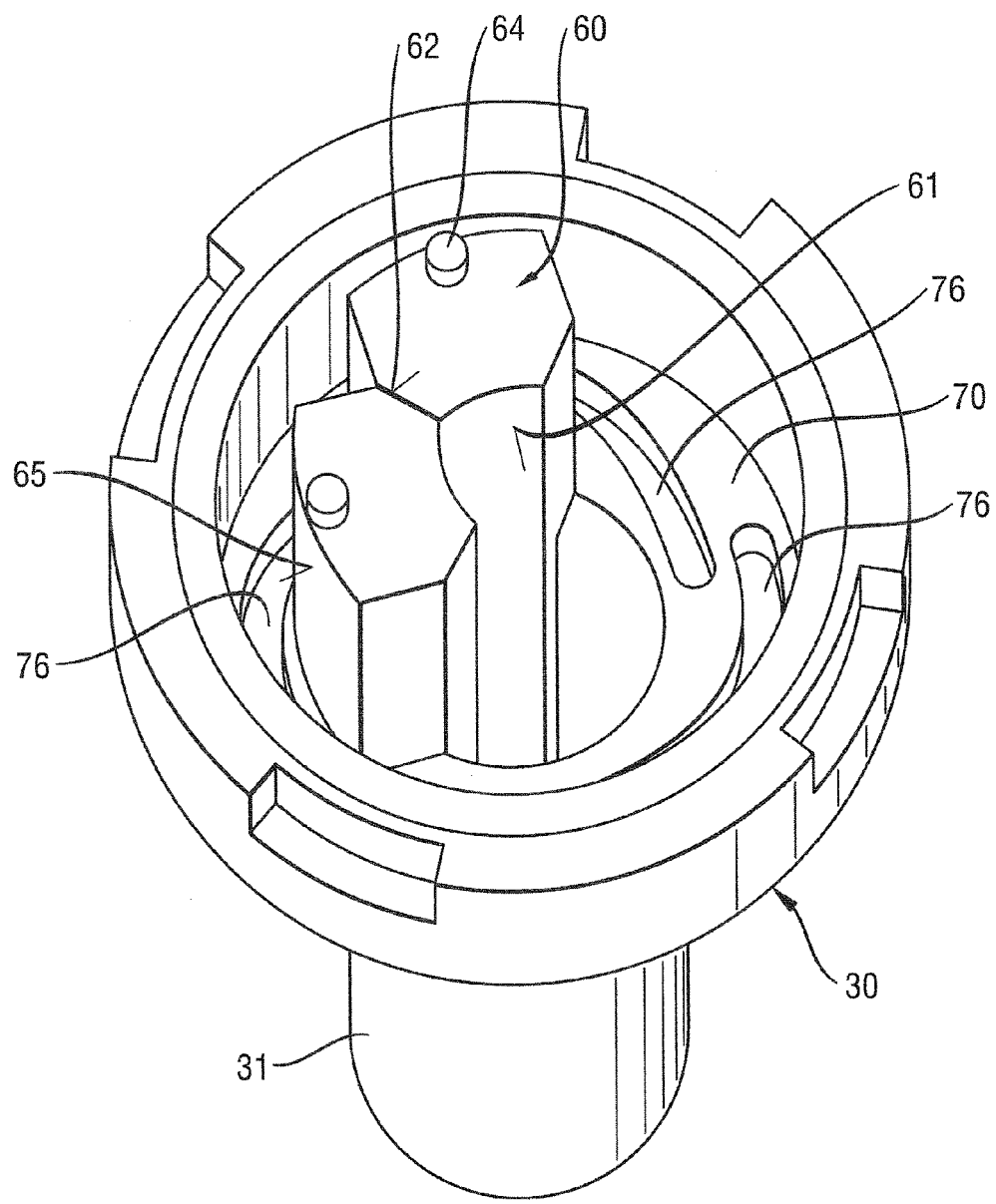
FIG. 5 shows a further perspective view of a partly opened drill guide of FIG. 2 with fewer parts.

As will be seen in connection with the explanation of FIGS. 4 and 5 the jaws 60 can be forced to move radially apart and this then forces the pins 64 in slots 34 away from the central axis 12 so that the internal cavity 49 widens and larger implants and drill bits can be introduced into the inner opening 35.

FIG. 4 shows a perspective view of a partly opened drill guide of FIG. 2, wherein the four jaws 60 are in the same position as shown in FIG. 3. Each jaw 60 is—in a view from above or in a cross section provided—a six sided kind of "polygon", wherein the inner jaw surface 61 as guide surface is concave and the outer jaw surface 65 is convex.

It can be seen from FIG. 4, that the jaw actuating pins 64 are rounded cylinders adapted to engage complementary oblong guide slots 34 which are oriented radially in the adjustment cap (not shown in FIG. 4). The jaws 60 are received in jaw reception recesses 36 provided at the inner circumference of the drill guide head 30.

Figure 6:
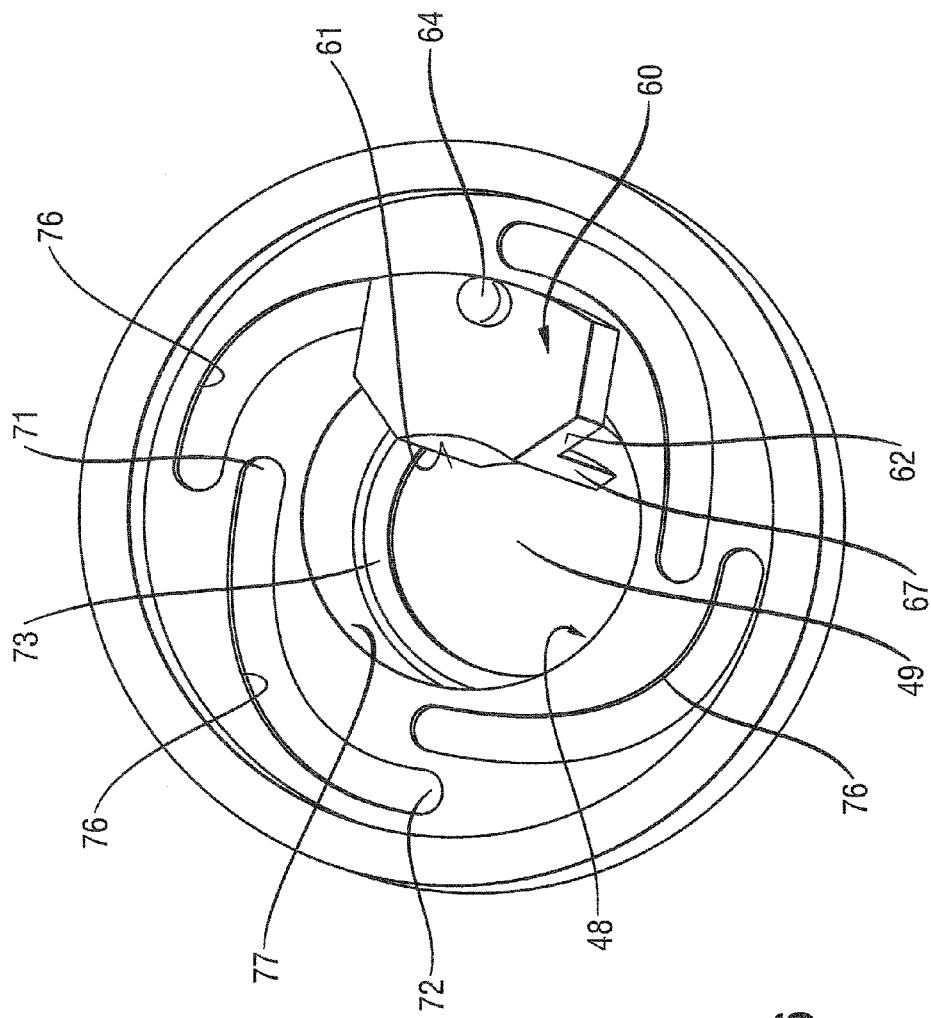
FIG. 6 shows a view from above on the drill guide body from FIG. 5 with even less elements of the drill guide than in FIG. 5.

FIG. 5 shows a further perspective view of a partly opened drill guide of FIG. 2 and FIG. 6 shows a view from above on this drill guide showing fewer parts. FIG. 5 shows the drill guide without the handle 20 and its handle attachment flange 21. Therefore the drill guide sleeve 31 extends beyond the drill guide head 30. The drill guide sleeve is fixedly connected to the drill guide plate 70 but in other embodiments these parts can also be separated. Drill guide plate 70 comprises an upper reception surface within which four grooves 76 are provided which are better represented in FIG. 6. The number of grooves 76 is identical to the number of jaws 60. Each jaw 60, as can be seen from FIGS. 9 to 11 has a slide block 66 on the underside of its main body adapted to engage one groove 76.

Upon rotation of the four jaws 60 through rotation of the adjustment cap 33 slide blocks 66 of each jaw 60 (shown in FIG. 10) move from an innermost position at the inner end 71 of groove 76 through the curved surface to the outer groove end 72. While this happens, jaw 60 also travels radially from an inner position as shown in FIGS. 4 and 6 to an outer position (not shown in the drawings) matching bore 35.

The orientation of the groove 76 in the embodiment shown starts with a slightly curved slot at the smallest distance from the centre of the device with a growing curvature until about to two third of its lengths when it turns around into an almost tangential direction until it ends at the outer end 72 of groove 76. The choice of the curvatures follows the possible sizes of the drill bits and implants used in connection with this drill guide and provide good functionality for the intended rotation. As can be seen from FIG. 6, the outer groove end 72 is positioned radially above the inner groove end 71, which allows a longer adjustment way for the jaws 60. It is also possible to provide shorter straight grooves 76.

FIG. 6 further shows the drill guide plate 70 having a smaller inner opening 77 ending with an inwardly extending lower flange shoulder 73 at the lower opening 48 attached to this body 70. The jaw body 87 (FIG. 10) is positioned above the groove 76 wherein the guiding extension 67 of the jaws 60 extend into inner opening 77 and beyond.

Figure 7:
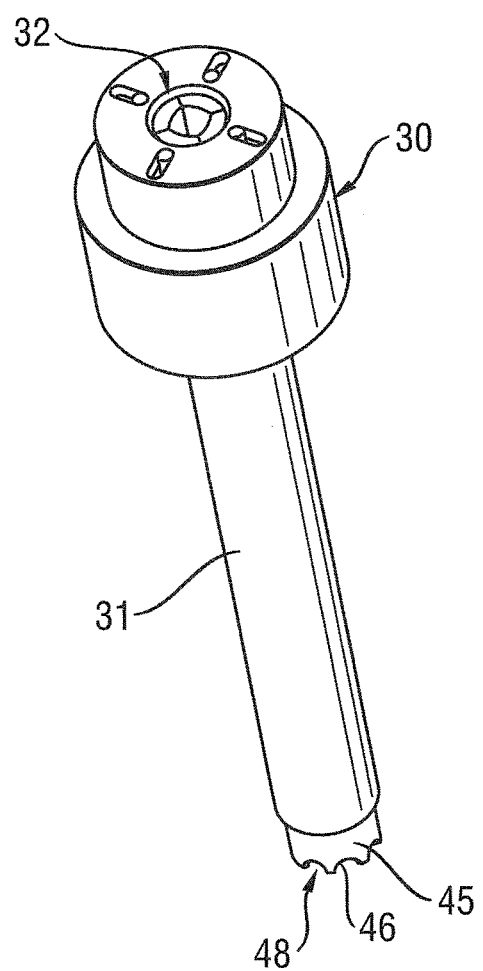
FIG. 7 shows a schematic view of the soft tissue protector and drill guide of FIG. 2.
Figure 8:
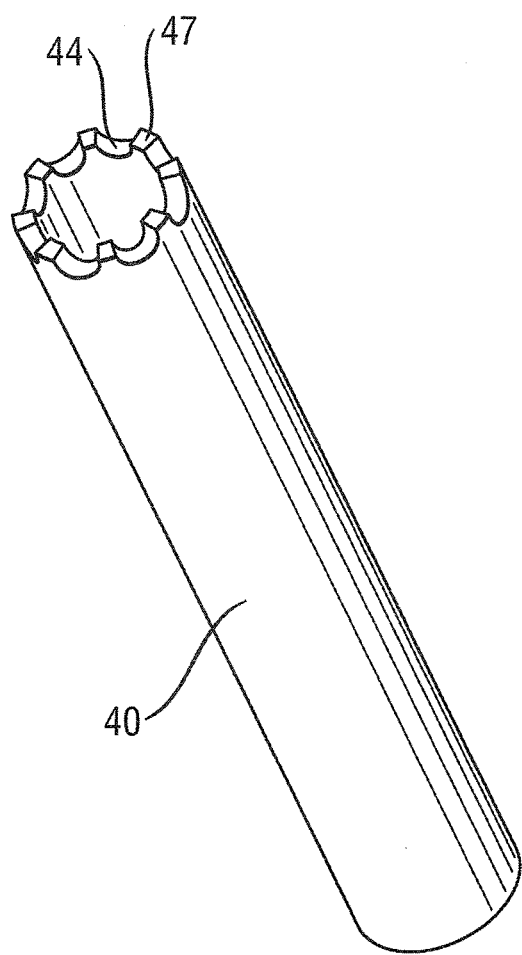
FIG. 8 shows the extension for the drill guide as already depicted in FIG. 2.

FIG. 7 shows a schematic view of the drill guide of FIG. 2 and FIG. 8 shows the extension 40 for the drill guide as already depicted in FIG. 2. Drill guide head 30 being one single part with drill guide body is fixedly connected with the drill guide sleeve 31 having its lower end connecting embossments 45 on the circumference of the sleeve 31 as well as intermediate grooves 46. In a different embodiment, it is possible to provide drill guide head 30 and drill guide body as two separate elements which are mounted together.

Extension 40, shown in FIG. 8, can be attached to the sleeve 31 through teeth or mating embossments 45 enter into mating grooves 44 and the same teeth 47 can, as seen in FIG. 2, be used as indentations touching the bone.

Figure 9:
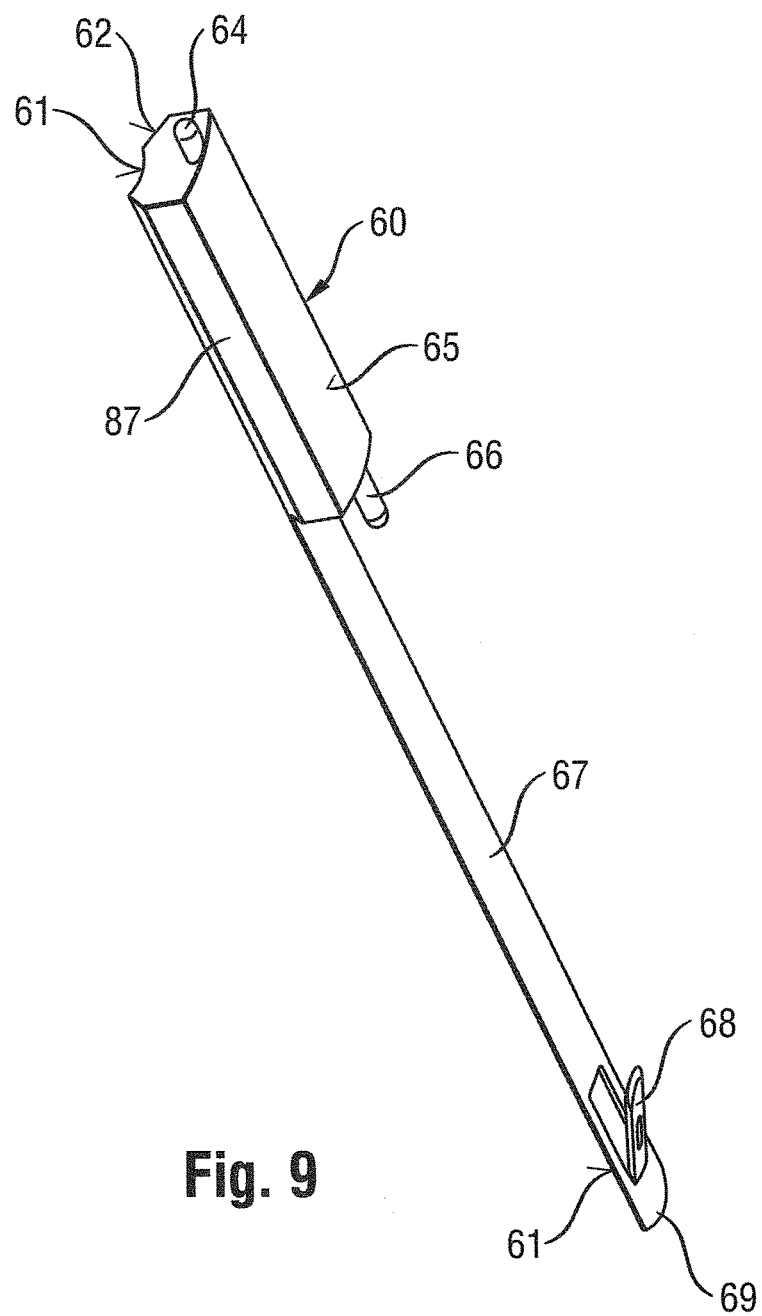
FIG. 9 shows a perspective view of one single jaw of the drill guide of FIG. 2.
Figure 10:
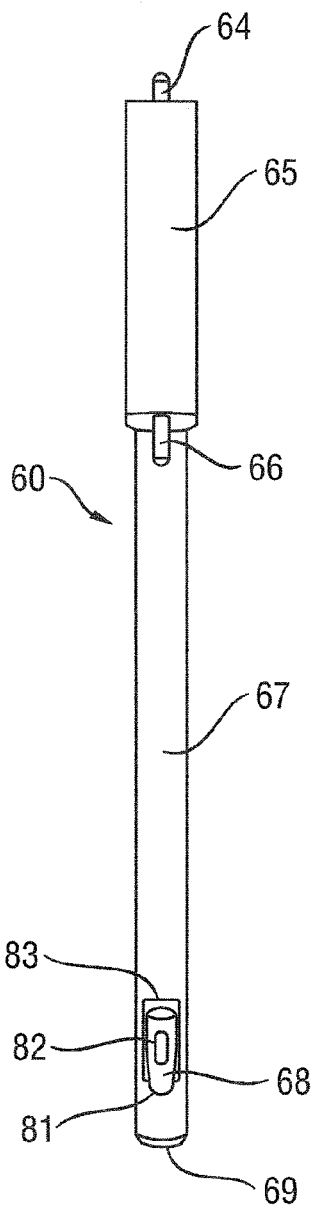
FIG. 10 shows a front view of the jaw of FIG. 9.
Figure 11:
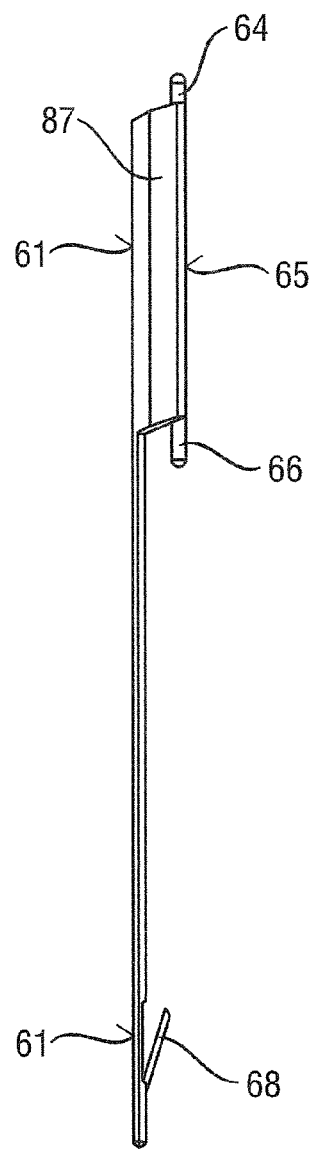
FIG. 11 shows a side view of the jaw of FIG. 9.

FIG. 9 shows a perspective view of one single jaw 60 of the drill guide of FIG. 2; wherein FIG. 10 shows a front view of the jaw 60 of FIG. 9 and FIG. 11 shows a side view of jaw 60.

The description relating to FIGS. 3 to 8 mainly reflected the positioning of the jaw body 87 with its jaw actuating pin 64 on the upper side and the slide block 66 on the lower side. FIG. 9 shows a perspective view slightly from behind with the outer jaw surface 65 wherein the guiding surface 61 as inner jaw surface is oriented away from the viewer. The jaw body extends below through the guiding extension 67 which is a thinner part. Preferably the jaw 60 is made of metal and the guiding extension 67 is simply a unitary extension of the guide body 87 having thus flexibility and the extension 67 is resilient. In fact, the curved concave inner guiding surface 61 is continuous and is prolonged as the inner curved surface of the guiding extension 67. This guiding extension 67 ends in the lower free end 69. Quite near to free end 69 a guide spring 68 is provided on the outer surface of the guiding prolongation opposite to the inner jaw surface 61. In the view from behind in FIG. 10 it can be seen that guide spring 68 is attached at a transmission edge 81 near the free end 69 and extends in direction of the jaw body 87. Guide spring 68 slightly enlarges towards its free end. It comprises a longitudinally oriented slit 82.

From FIG. 10 can be seen, that said guide spring 68 is positioned within a rectangular recess 83 and can be fabricated out of the material of recess 83, especially punched out as a unitary piece. The recess 83 provides a place where the spring 68 can be located, when the moving planes are completely apart. When the jaw 60 is positioned within the drill guide, the guiding extension 67 is positioned within the drill guide sleeve and the springs 68 always push the guiding extension 67 one towards another so that without an introduced drill bit or implant the lower portions of the guiding extension 67 are also engaging one another as with the contacting jaw surfaces 62. This is independent from the actual position of the different jaw bodies 87 in a radial relationship. However, upon reception of a larger diameter drill bit or implant from the opening 32 the resilient extension 67 are pushed away one from another against the force of the springs 68. Springs 68 are contacting the inner wall of the drill guide sleeve 31 and are pushing the inner jaw surfaces 61 of the flexible guiding extension 67 one against the other, allowing passage of said elements against the action of the springs 68.

It is also possible that, If the upper jaws 61 are open, the lower inner surfaces 61 have the same distance one from another when they are stiff, in this case the springs 68 do not press these surfaces together and close them at the extension free end 69.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A soft tissue protector and drill guide for guiding elements of an implantation kit during a surgical intervention, comprising:
    a soft tissue protector main body extending along a central longitudinal axis,
    a gripping portion attached to the soft tissue protector main body;
    an adjustment cap rotatably mounted on the main body, the adjustment cap having a plurality of radially extending slots;
    a guide plate fixed to the main body and spaced from the adjustment cap along the central longitudinal axis, the guide plate having a plurality of arcuate circumferentially extending slots formed therein;
    a plurality of jaws defining a through going cavity along the central longitudinal axis of the soft tissue protector main body, the jaws having inner jaw surfaces, each jaw having an upper and a lower surface, each upper and lower surface having an axially extending pin extending outwardly therefrom;
    wherein the through going cavity has an upper and a lower opening for receiving the element to be guided,
    wherein the axially extending pin on the upper surface of each of the jaws engages the radial slots in the adjustment cap and the axially extending pin on the lower surface of each jaw engages the arcuate circumferential slots in the guide plate;
    wherein the soft tissue protector main body has a lower contact surface to be positioned on an object on or into which said element of the implantation kit is to be guided;
    wherein the adjustment cap can be rotated against the soft tissue protector main body causing the axially extending pins in the upper and lower surface to move radially in the respective slots in the adjustment cap and guide plate forcing the jaws radially apart providing a diameter which can be varied of the through going cavity with the inner jaw surfaces; and
    each jaw comprises a flexible guiding extension that ends near the lower opening of the drill guide and extends along a longitudinal axis, wherein the flexible guiding extension comprises, adjacent a free end of the guiding extension, a guide spring formed from the guiding extension and oriented away from the longitudinal axis of the guiding extension, the guide spring contacting an inner wall of the soft tissue protector main body and pushing the inner jaw surfaces of the flexible guiding extension towards the central longitudinal axis of the soft tissue protector main body while allowing passage of said elements against the action of the spring.

2. The soft tissue protector and drill guide according to claim 1, wherein the elements of an implantation kit are drill bits and implants.

3. The soft tissue protector and drill guide according to claim 1, wherein each jaw comprises a stiff upper jaw body being radially guided in the rotatable adjustment cap and connected to the flexible extension.

4. The soft tissue protector and drill guide according to claim 1, wherein the soft tissue protector and drill guide comprises at least three jaws.

5. The soft tissue protector and drill guide according to claim 1, wherein when the jaws are in an innermost position, side walls of adjacent jaw bodies contact each other, thus providing a completely surrounded inner through going cavity.

6. A soft tissue protector and drill guide for guiding elements of an implantation kit during a surgical procedure comprising:
    a tubular main body having first and second open ends extending along a central longitudinal axis;
    at least three jaws mounted within the tubular main body at the first end thereof, the jaws selectively moveable in a radial direction towards and away from the central longitudinal axis to vary an opening in the main body;
    a cap rotatably mounted on the tubular body, the cap having a radial drive element engaging a first axially extending drive element on each jaw of the at least three jaws for moving the jaws in the radial direction towards and away from the central longitudinal axis to thereby vary an opening at the first end of the main body;
    a guide plate having arcuate guide elements for guiding a second axially extending guide element on each jaw, the guide plate spaced away from the rotatable cap along the central longitudinal axis; and
    each jaw having a flexible guiding extension portion extending towards the second end of the main body, each extension portion having a spring formed thereon adjacent a free end thereof and engaging the tubular main body and biasing the extensions inwardly towards the central longitudinal axis and centering the elements of the implantation kit at the second end of the tubular main body.

7. The soft tissue protector and drill guide according to claim 6, wherein each flexible guiding extension portion ends before the second opening of the drill guide and extends along a longitudinal axis, wherein the flexible guiding extension portion comprises, at the free end of the guiding extension, the spring oriented away from the longitudinal axis of the guiding extension, the spring contacting the inner wall of the tubular main body and pushing the inner jaw surfaces of the flexible guiding extension one against the other, allowing passage of said elements of the implantation kit against the action of the spring.

8. The soft tissue protector and drill guide according to claim 7, wherein each jaw comprises a stiff upper jaw body being radially guided in the rotatable cap and connected to the flexible guiding extension portion.

9. The soft tissue protector and drill guide according to claim 8, wherein each upper jaw body comprises the first axially extending drive element, wherein the rotatable cap provides the opening at the first end and comprises the radial drive element for each first axially extending drive element of the jaws engaging the first axially extending drive element for providing a movement of the jaw bodies against the tissue protector main body when the cap is rotated.

10. The soft tissue protector and drill guide according to claim 9, wherein the first axially extending drive element is a pin and the radial drive element for each pin is a radially oriented slot engaging each pin for allowing the radial movement of the jaw during movement of the jaw bodies.

11. The soft tissue protector and drill guide according to claim 6, wherein when in an innermost position, the walls of adjacent jaw bodies contact each other, thus providing a completely surrounded inner through going opening.

12. A soft tissue protector and drill guide for guiding elements of an implantation kit during a surgical procedure comprising:
- a tubular main body having first and second open ends extending along a central longitudinal axis;
- at least three jaws mounted within the tubular main body at the first end thereof, the jaws selectively moveable in a radial direction towards and away from the central longitudinal axis to vary an opening in the main body;
- a cap rotatably mounted on the main body, the cap having a drive element engaging each jaw of the at least three jaws for moving the jaws in the radial direction towards and away from the central longitudinal axis to thereby vary the opening in the main body;
- a guide plate;
- wherein each jaw comprises a first axially extending pin extending towards the first open end of the tubular body, wherein each drive element comprises a radially extending slot for guiding each first axially extending pin of each jaw, allowing for a radial movement of the jaws, and a second axially extending pin on each jaw extending towards the second end of the tubular body engaging an arcuate slot in the guide plate fixed to the tubular body and axially spaced from the radial slot towards the second open end of the body for moving each jaw in a radial direction by rotation of the rotatable cap about the central longitudinal axis;
- each jaw having a flexible guiding extension portion extending towards the second end of the tubular main body, each extension portion biased inwardly towards the central longitudinal axis and capable of centering the elements of the implantation kit at the second end of the tubular main body; and
- wherein each flexible guiding extension portion ends before the second open end of the tubular main body, wherein the flexible guiding extension portion comprises, adjacent a free end of the guiding extension, a guide spring oriented away from a longitudinal axis of the guiding extension, the guide spring contacting the inner wall of the tubular main body and pushing the inner surfaces of the flexible guiding extension one against the other, allowing passage of said elements of the implantation kit against the action of the spring; and
- wherein each jaw comprises an upper jaw body being radially guided in the tubular main body, each jaw axially extended by the first and second pins respectively engaging the radially extending and arcuate slots, and connected to the flexible guiding extension portion.

* * * * *